(12) United States Patent
Busch et al.

(10) Patent No.: US 6,627,643 B2
(45) Date of Patent: Sep. 30, 2003

(54) METHODS FOR PREPARING SODIUM-HYDROGEN EXCHANGER TYPE-1 INHIBITORS

(75) Inventors: Frank R. Busch, Gales Ferry, CT (US); Gregory J. Withbroe, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/320,186

(22) Filed: Dec. 16, 2002

(65) Prior Publication Data

US 2003/0119873 A1 Jun. 26, 2003

Related U.S. Application Data

(60) Provisional application No. 60/342,888, filed on Dec. 19, 2001.

(51) Int. Cl.⁷ .................. A61K 31/4709; A61K 31/415; C07D 401/04; C07D 231/12
(52) U.S. Cl. .................. 514/314; 514/406; 546/167; 548/369.7
(58) Field of Search ................. 514/314, 406; 546/167; 548/369.7

(56) References Cited

U.S. PATENT DOCUMENTS

2002/0082274 A1   6/2002   Lambert et al. ............ 514/307

FOREIGN PATENT DOCUMENTS

WO   9943663   9/1999

OTHER PUBLICATIONS

Weidenhagen, R. et al., 1939, pp. 2010–2020.
Bream, et al., Arzneim. Forsch.(Drug Res.),25(10), 1975, pp. 1477–1482.
Menozzi, et al., J. Heterocyclic Chem., 24, 1987, pp. 1669–1675.
Ferlin, et al., IL Farmaco, 44(12), 1989, pp. 1141–1155.
Baumgarth, et al., J. Med. Chem., 40, 1997, pp. 2017–2034.

*Primary Examiner*—Patricia L. Morris
(74) *Attorney, Agent, or Firm*—P. C. Richardson; P. H. Ginsburg; R. L. Catania

(57) ABSTRACT

This invention relates to methods of preparing sodium-hydrogen exchanger type 1 (NHE-1) inhibitors of formula I'

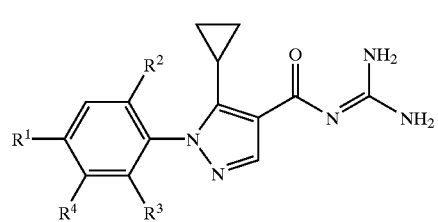

I' and methods of preparing pharmaceutical compositions comprising such NHE-1 inhibitors.

13 Claims, No Drawings

METHODS FOR PREPARING SODIUM-HYDROGEN EXCHANGER TYPE-1 INHIBITORS

This application claims priority from U.S. provisional application No. 60/342,888, filed Dec. 19, 2001.

FIELD OF THE INVENTION

This invention relates to methods of preparing sodium-hydrogen exchanger type 1 (NHE-1) inhibitors and methods of preparing pharmaceutical compositions comprising the NHE-1 inhibitors.

BACKGROUND OF THE INVENTION

Sodium-hydrogen exchanger type 1 (NHE-1) inhibitors of formula I'

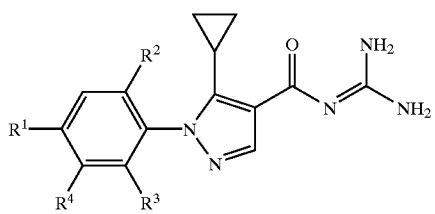

are useful for the prevention and treatment of myocardial ischemic injury. Myocardial ischemic injury can occur in out-patient as well as in perioperative settings and can lead to the development of sudden death, myocardial infarction or congestive heart failure. It is anticipated that therapies using the NHE-1 inhibitors of formula I' will be life-saving and reduce hospitalizations, enhance quality of life and reduce overall health care costs of high risk patients.

Commonly assigned WO 99/43663A1, discloses a variety of NHE-1 inhibitors including NHE-1 inhibitors relating to the methods of the present invention.

Baumgarth, et al. (1997) *J. Med. Chem.* 40, 2017–2034 discloses synthesizing acyl guanidine via coupling of an ester and guanidine, in addition to an acid chloride and guanidine wherein the substrates are aromatic monocyclic structures.

Ferlin, et al. (1989) *Il Famraco* 44:12, 1141–1156 disclose a method of synthesizing 5-hydrazinoquinoline by reacting quinolin-5-ylamine with stannous chloride and sodium nitrite.

Colored impurities are produced when N-(5-cyclopropyl-1-quinolin-5-yl-1H-pyrazole-4-carbonyl)-guanidine, an NHE-1 inhibitor of formula I', is prepared by the previously known processes. For example, aqueous solutions of N-(5-cyclopropyl-1-quinolin-5-yl-1H-pyrazole-4-carbonyl)-guanidine made by the previously known processes have a distinct yellow color. The impurities responsible for such coloration have not been identified.

From a commercial and regulatory point of view, discoloration of pharmaceutical products containing N-(5-cyclopropyl-1-quinolin-5-yl-1H-pyrazole-4-carbonyl)-guanidine is undesirable. In the case of pharmaceutical products that are administered to patients, especially those administered by injection, it is considered commercially advantageous that such products be substantially colorless and in as pure a form as possible. For example, a colorless product is helpful for conducting blinded clinical research using a placebo, ensuring that the placebo is visually indistinguishable from the active product.

SUMMARY OF THE INVENTION

This invention provides improved processes for preparing NHE-1 inhibitors of formula

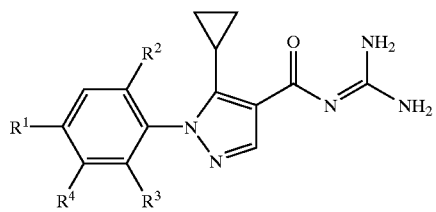

wherein $R^1$ is methylsulfonyl or hydrogen, $R^2$ is hydrogen or a halogen, $R^3$ is hydrogen, $R^4$ is hydrogen or a halogen, or $R^3$ and $R^4$, together with the carbon atoms to which they are attached, form a six member fully unsaturated ring having one hetero atom that is nitrogen.

In one aspect, this invention provides methods of preparing a compound of formula I'

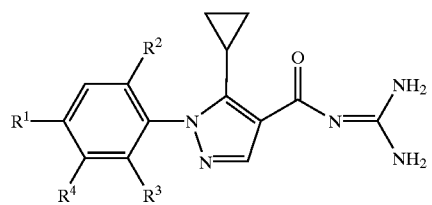

comprising: combining a mixture of acetonitrile and a compound of formula IX'

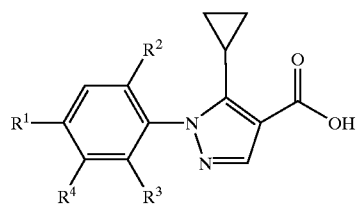

with thionyl chloride to form a mixture comprising a compound of formula X';

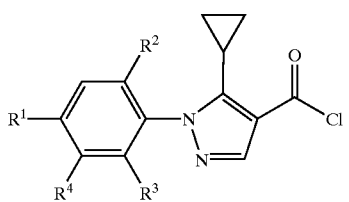

evaporating excess thionyl chloride from said mixture to form an evaporated mixture; and combining said evaporated mixture with guanidine to form a compound of formula I', wherein $R^1$ is methylsulfonyl or hydrogen, $R^2$ is hydrogen or a halogen, $R^3$ is hydrogen, $R^4$ is hydrogen or a halogen, or $R^3$ and $R^4$ form, together with the carbon atoms to which they are attached, a six member fully unsaturated ring having one hetero atom that is nitrogen.

In another aspect, the invention provides methods of preparing a pharmaceutical composition comprising: combining a mixture of acetonitrile and a compound of formula IX'

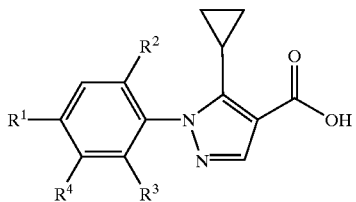

with thionyl chloride to form a mixture comprising a compound of formula X';

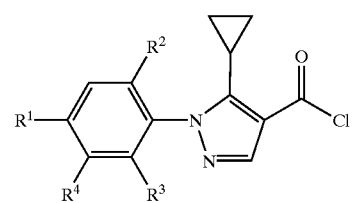

evaporating of excess thionyl chloride from said mixture to form an evaporated mixture; combining said evaporated mixture with guanidine to form a final mixture comprising a compound of formula I'

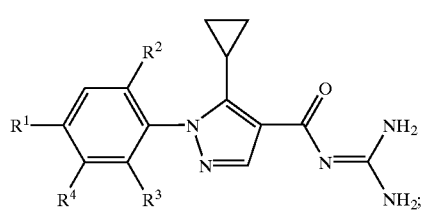

isolating said compound of formula I' from said final mixture; and combining said compound of formula I', or a pharmaceutically acceptable salt thereof, with a pharmaceutically acceptable vehicle, diluent or carrier, wherein $R^1$ is methylsulfonyl or hydrogen, $R^2$ is hydrogen or a halogen, $R^3$ is hydrogen, $R^4$ is hydrogen or a halogen, or $R^3$ and $R^4$ form, together with the carbon atoms to which they are attached, a six member fully unsaturated ring having one hetero atom that is nitrogen.

In a preferred embodiment of the invention, the compound of formula IX' is 5-cyclopropyl-1-quinolin-5-yl-1H-pyrazole-4-carboxylic acid, the compound of formula X' is 5-cyclopropyl-1-quinolin-5-yl-1H-pyrazole-4-carbonyl chloride and the compound of formula I' is N-(5-cyclopropyl-1-quinolin-5-yl-1H-pyrazole-4-carbonyl)-guanidine.

In a more preferred embodiment, the 5-cyclopropyl-1-quinolin-5-yl-1H-pyrazole-4-carboxylic acid in acetonitrile is combined with thionyl chloride at a temperature of about 25° C. for at least about one hour and preferably for at least about one-half hour.

In another preferred embodiment, the evaporation of thionyl chloride reduces the volume of the mixture by about 10%. More preferably, said evaporation is performed under vacuum and at a temperature of about 85° C.

Unless otherwise defined below, all technical and scientific terms used herein have the same meanings as commonly understood by one of ordinary skill in the art to which this invention belongs.

"Halogen" means an atom of one of the elements of Group 18 of the periodic table of elements, preferably fluorine, bromine or chlorine.

"Pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate. Where more than one basic moiety exists, multiple salts (e.g., di-salt) are included. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

Those skilled in the art will recognize, based on the present description, that certain compounds of this invention will contain one or more atoms that may be in a particular stereochemical or geometric configuration, giving rise to stereoisomers and configurational isomers. All such isomers and mixtures thereof are included in this invention.

DETAILED DESCRIPTION OF THE INVENTION

Reaction Scheme A illustrates processes of preparing compounds of formula VI'. Scheme B illustrates processes of preparing compounds of formula I' using compounds of formula VI' from Scheme A. These processes are used to make NHE-1 inhibitors, including, for example, N-(5-cyclopropyl-1-quinolin-5-yl-1H-pyrazole-4-carbonyl)-guanidine.

SCHEME A

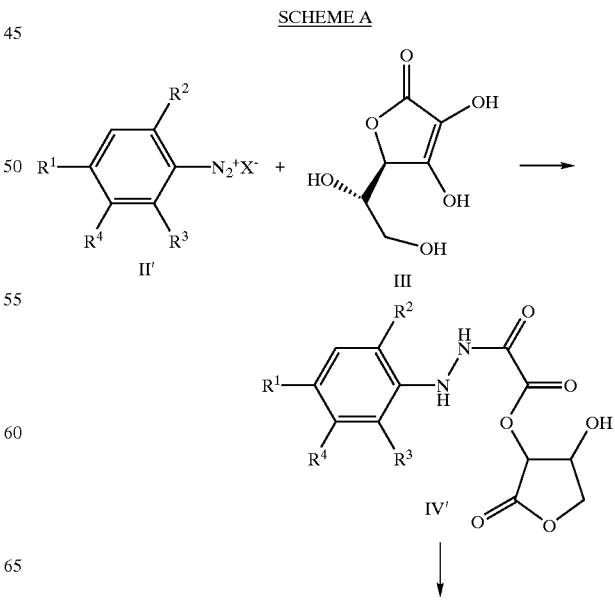

-continued

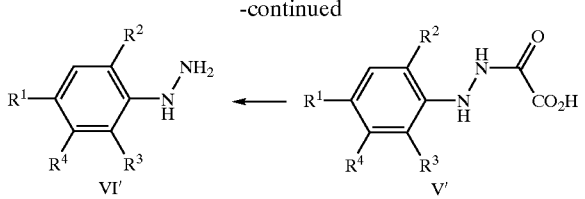

SCHEME B

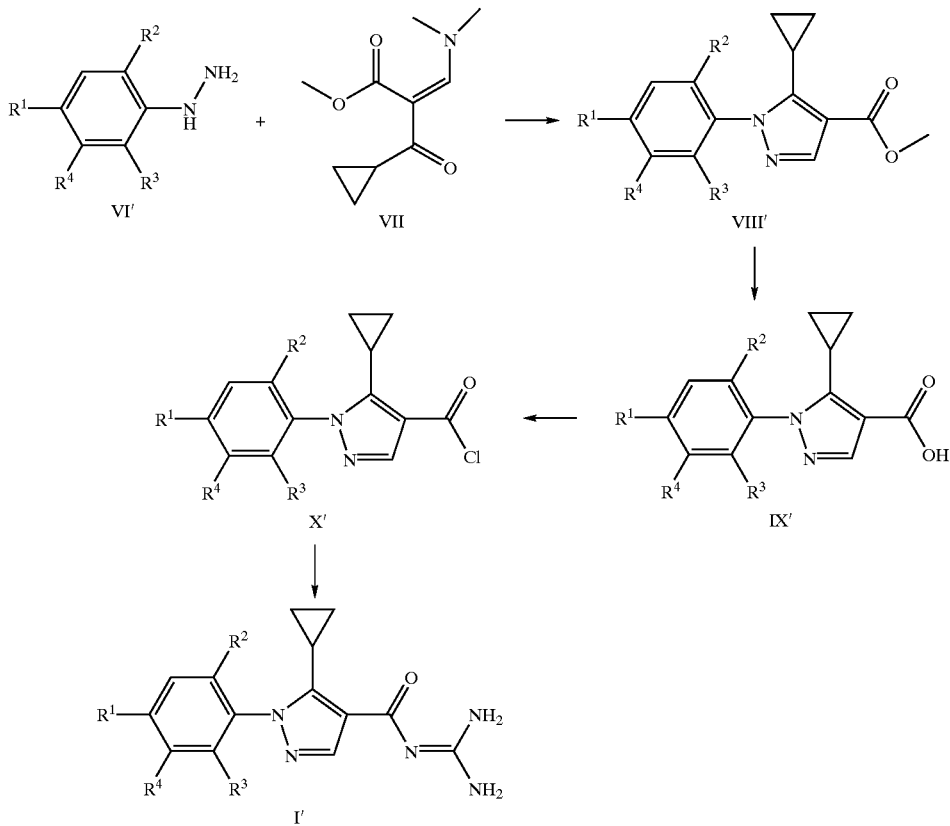

Scheme B illustrates the process of preparing a compound of formula I'. A hydrazino compound of formula VI' is combined with the compound of formula VII in an inert solvent such as, for example, ethyl acetate at a temperature of about 20° C. for about one hour followed by heating to a temperature of about 75° C. for about five hours to form a pyrazole compound of formula VIII'.

The compound of formula VII may be prepared by combining methyl-3-cyclopropyl-3-oxopropanoate in ethyl acetate with N,N-dimethylformamide dimethylacetal at a temperature of about 65° C. to about 75° C. for about 4 hours.

A pyrazole compound of formula VIII' is then hydrolyzed with a base, such as, for example, sodium hydroxide, lithium hydroxide or potassium hydroxide, in a solvent such as water and/or methanol and/or THF at ambient temperature or at an elevated temperature (e.g., reflux) for about one hour to about five hours to prepare an acid of formula IX'.

An acid of formula IX' is activated with a coupling agent such as thionyl chloride at an elevated temperature of about 60° C. to about 90° C. for about 13 hours to form the acid chloride compound of formula X'. Those skilled in the art will appreciate, based upon the present description, that other suitable coupling agents may be used. A suitable coupling agent is one which transforms the carboxylic acid into a reactive species which forms an acyl guanidine on reaction with guanidine. The coupling agent can convert the carboxylic acid to an activated intermediate which is isolated and/or formed in a first step and allowed to react with guanidine in a second step. Examples of such coupling According to Scheme A, a diazonium salt of a compound of formula II' is combined with L-ascorbic acid (formula III) to form a lactone intermediate compound of formula IV' as a transient intermediate, which decomposes to an oxalic acid intermediate compound of formula V'. At elevated reaction temperatures, above about 35° C. and preferably above about 50° C. and most preferably above about 80° C., a compound of formula IV' converts to a formula VI' compound as a one-pot reaction. At lower temperatures, the oxalic acid intermediate compounds of formula V' are not converted to compounds of formula VI'. An oxalic compound of formula V' may be converted to a hydrazino compound of formula VI' using a hydrolyzing agent, preferably hydrochloric acid. Using concentrated hydrochloric acid will result in formation of a compound of formula VI' as the hydrochloride salt.

As noted above, the lactone intermediates of formula IV' are unstable and decompose under the reaction conditions into the corresponding oxalic acid derivative. However, when the diazonium salt of formula II' is derived from 2,5-dichlorophenylaniline, the lactone intermediate may be isolated.

agents and activated intermediates include thionyl chloride or oxalyl chloride to form the acid chloride, cyanuric flouride to form an acid flouride or an alkyl chloroformate such as isobutyl or isopropenyl chloroformate or propanephosphonic anhydride to form a mixed anhydride of the carboxylic acid, or carbonyldimidazole to form an acylimidazole. Alternatively, the coupling agent may be a reagent which effects coupling in a one pot process. Exemplary coupling reagents are 1-(3-dimethylaminopropyl)-3-ethylcarbodiimide hydrochloride-hydroxybenzotriazole (EDC/HOBT), dicyclohexylcarbodiimide/hydroxybenzotriazole (DCC/HOBT),2-ethoxy-1-ethoxycarbonyl-,2dihydroquinoline (EEDQ) and diethylphosphoryl-cyanide. The coupling is performed in an inert solvent, preferably an aprotic solvent, in the presence of excess guanidine. Exemplary solvents include acetonitrile, dichloromethane, dimethylformamide and chloroform or mixtures thereof. Use of these coupling agents and appropriate selection of solvents and temperatures are known to those skilled in the art, based upon the present description, or can be readily determined from the literature in light of this disclosure. These and other exemplary conditions useful for coupling carboxylic acids are described, for example, in Houben-Weyl, Vol XV, part II, E. Wunsch, Ed., G. Theime Verlag, 1974, Stuttgart; M. Bodansky, Principles of Peptide Synthesis, Springer-Verlag, Berlin 1984; and The Peptides, Analysis, Synthesis and Biology (ed. E. Gross and J. Meienhofer), vols 1–5 (Academic Press, NY 1979–1983).

A compound of formula X' is coupled with guanidine to form the NHE-1 inhibitor of formula I' by combining a formula X' compound with guanidine hydrochloride and an inorganic base, such as sodium hydroxide, lithium hydroxide or potassium hydroxide, in a solvent which is preferably selected from water, methanol and tetrahydrofuran.

In a preferred embodiment of the reactions of Scheme A and Scheme B, the formula II' compound is a diazonium salt of 5-aminoquinoline. The diazonium salt of 5-aminoquinoline is combined with ascorbic acid to form the compound of formula VI' that is 5-hydrazinoquinoline. The pyrazole compound of formula VIII' that is formed is 5-cyclopropyl-1-quinolin-5-yl-1H-pyrazole-4-carboxylic acid methyl ester.

Prior to the coupling step with guanidine, 5-cyclopropyl-1-quinolin-5-yl-1H-pyrazole-4-carboxylic acid methyl ester is preferably treated with citric acid to remove red impurities. In this treatment, the solvent solution containing 5-cyclopropyl-1-quinolin-5-yl-1H-pyrazole-4-carboxylic acid methyl ester is combined with an aqueous solution of citric acid to form a darker red aqueous layer and a red organic layer. The aqueous layer is discarded, leaving the organic layer containing citric acid purified 5-cyclopropyl-1-quinolin-5-yl-1H-pyrazole-4-carboxylic acid methyl ester.

5-Cyclopropyl-1-quinolin-5-yl-1H-pyrazole-4-carboxylic acid methyl ester is hydrolyzed with a base such as sodium hydroxide in water to form 5-cyclopropyl-1-quinolin-5-yl-1H-pyrazole-4-carboxylic acid, analogous to an acid of formula IX'.

5-Cyclopropyl-1-quinolin-5-yl-1H-pyrazole-4-carboxylic acid is then activated with a coupling agent such as thionyl chloride to form the chloride compound, analogous to the formula X' compound. For the activation reaction, 5-cyclopropyl-1-quinolin-5-yl-1H-pyrazole-4-carboxylic acid is combined with dry acetonitrile to form a slurry. Thionyl chloride is added to the slurry and the mixture is heated to about 25° C. preferably for at least about one-half hour, more preferably for at least about one hour. Unreacted thionyl chloride and dissolved HCl gas is then removed by atmospheric distillation. Preferably, the volume of the mixture is reduced by about 10%. The resulting slurry containing the chloride activated compound of formula X' is then coupled with guanidine to form the NHE-1 inhibitor, N-(5-cyclopropyl-1-quinolin-5-yl-1H-pyrazole-4-carbonyl)-guanidine. For coupling reaction the slurry is added to an aqueous guanidine solution at pH 14.

Those skilled in the art will appreciate, based upon the present disclosure, that the use of acetonitrile in the chloride activation reaction is particularly advantageous for a commercial production process in that the required reaction time with thionyl chloride is relatively short, i.e. approximately one-half to one hour. Likewise, the removal of thionyl chloride by distillation following formation of the chloride compound is advantageous in that it eliminates the cumbersome additional step of isolating the activated chloride compound prior to the guanidine coupling reaction to form the NHE-1 inhibitor. Moreover, it will be appreciated that the distillation step also eliminates the need to use a second solvent for resuspension of the recovered chloride for use in the guanidine coupling reaction.

N-(5-Cyclopropyl-1-quinolin-5-yl-1H-pyrazole-4-carbonyl)-guanidine prepared by a method of this invention may be converted to a pharmaceutically acceptable salt. For example N-(5-cyclopropyl-1-quinolin-5-yl-1H-pyrazole-4-carbonyl)-guanidine may be converted to its mesylate salt, for example, by combining the compound with methanesulfonic acid, preferably in a suitable polar aprotic solvent at a temperature of about 40° C. to about 80° C. Suitable polar aprotic solvents preferably include a mixture of acetone and 1-methyl-2-pyrrolidonone. Conversion to other pharmaceutically acceptable salts may be performed using processes known in the art, based upon the present description.

N-(5-Cyclopropyl-1-quinolin-5-yl-1H-pyrazole-4-carbonyl)-guanidine monomesylate, when prepared by the chemical processes and methods described above, gives rise to a 1% aqueous solution having very low blue light absorption. For example, at 450 nm the light absorption of a 1% solution is in the range 0.007–0.005. As noted above, previous procedures give rise to distinctly yellow solutions with absorption levels in the range 0.027–0.025. Light absorption is calculated according to the formula, $A=\log_{10}(I_0/I)$, wherein "$I_0$" is incident light and "I" is transmitted light.

In another preferred embodiment, the formula II' compound is a diazonium salt of 2-chloro-4-methanesulfonyl-phenylamine. The diazonium salt is combined with ascorbic acid to form a compound of formula VI' that is 2-chloro-4-methanesulfonyl-2-phenylhydrazine. The formula VIII' pyrazole formed is 5-cyclopropyl-1-(2-chloro-4-methanesulfonylphenyl)-1H-pyrazole-4-carboxylic acid methyl ester.

5-Cyclopropyl-1-(2-chloro-4-methanesulfonylphenyl)-1H-pyrazole-4-carboxylic acid methyl ester is hydrolyzed with a base such as sodium hydroxide in water to form 5-cyclopropyl-1-(2-chloro-4-methanesulfonylphenyl)-1H-pyrazole-4-carboxylic acid, analogous to an acid of formula IX'. The carboxylic acid pyrazole is then activated with coupling agent such as thionyl chloride to form the activated compound, analogous to a compound of formula X'. The activated compound is then coupled with guanidine to form the NHE-1 inhibitor, N-{5-cyclopropyl-1-(2-chloro-4-methanesulfonylphenyl)-1H-pyrazole-4-carbonyl}-guanidine.

The starting material and reagents for the above described compounds are commercially available or can be easily synthesized by those skilled in the art using conventional methods of organic synthesis.

Administration of the compounds prepared by a method of this invention can be via any method which delivers a compound of this invention preferentially to the desired tissue (e.g., liver and/or cardiac tissues). These methods include, for example, oral routes, parenteral and intraduodenal routes. Generally, the compounds of the present invention may be administered in single (e.g., once daily) or multiple doses or via constant infusion.

The compounds prepared by a method of this invention are useful, for example, in reducing or minimizing damage effected directly to any tissue that may be susceptible to ischemia/reperfusion injury (e.g., heart, brain, lung, kidney, liver, gut, skeletal muscle, retina) as the result of an ischemic event (e.g., myocardial infarction). The compounds can be used to prevent (i.e. prospectively or prophylactically), blunt or stem, tissue damage (e.g., myocardial tissue) in patients who are at risk for ischemia (e.g., myocardial ischemia).

The compounds prepared by a method of this invention can be administered in any suitable manner, including, for example, orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician, based upon the present description.

The amount of administration as well as the timing of administration will be dependent on the subject being treated, on the severity of the affliction, on the intended manner of administration and on the judgement of the prescribing physician, based upon the present description. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases (e.g., cardiovascular disease).

For example, in one mode of administration, the compounds prepared by a method of this invention may be administered just prior to surgery (e.g., within twenty-four hours before surgery for example cardiac surgery) during or subsequent to surgery (e.g., within twenty-four hours after surgery) where there is risk of myocardial ischemia. The compounds may also be administered in a chronic daily mode.

Amounts of the compounds prepared by a method of this invention are used that are effective for ischemic protection. A preferred dosage is about 0.001 to 100 mg/kg/day of the compounds. An especially preferred dosage is about 0.01 to 50 mg/kg/day of the compounds.

The compounds of the present invention can be administered in the form of a pharmaceutical composition comprising at least one of the compounds of this invention together with a pharmaceutically acceptable vehicle, carrier or diluent. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions, for example, in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington: The Science and Practice of Pharmacy*, Mack Publishing Company, Easton, Pa., 19th Edition 1995.

Pharmaceutical compositions according to the invention may contain for example 0.0001%–95% of the compounds prepared by a method of this invention. In any event, the composition or formulation to be administered will contain a quantity of the compound(s) prepared according to the invention in an amount effective to treat the disease, condition or disorder of the subject being treated.

The disclosures of all patents, applications, publications and documents, for example brochures or technical bulletins, cited herein, are hereby expressly incorporated by reference in their entirety.

EXPERIMENTAL PROCEDURES

NMR spectra were recorded on a Varian XL-300 (Varian Co., Palo Alto, Calif.), a Bruker AM-300 spectrometer (Bruker Co., Billerica, Mass.) or a Varian Unity 400 at about 23° C. at 300 or 400 MHz for proton. Chemical shifts are expressed in parts per million downfield from trimethylsilane. The peak shapes are denoted as follows: s=singlet; d=doublet; t=triplet, q=quartet; m=multiplet; bs=broad singlet.

Example 1

5-Hydrazinoquinoline dihydrochloride

Concentrated hydrochloric acid (300 ml) was added to a one liter round-bottomed flask under a nitrogen atmosphere and equipped with mechanical stirrer, thermometer and reflux condenser. The reaction vessel was cooled to 0±2° C. and 5-aminoquinoline (50 g) was charged in one portion. An increase in temperature was observed from 0±2° C. up to 25–26° C. resulting in a pink suspension. The reaction mixture was again cooled to 0±2° C. and a solution of sodium nitrite (29 g) in water (50 ml) was added to the reaction vessel over a period of 30 minutes, while maintaining the temperature at 0±2° C. The reaction was stirred for 1 hour at 0±2° C. Then, L-ascorbic acid (50 g) was added portionwise over a period of 30 minutes. The addition of the first portion of L-ascorbic (1–2 grams) led to effervescence, while the next portions (about 5 grams each) could be added faster as effervescene was not significant. The reaction mixture (brown-red suspension) was stirred at 0±2° C. for 5–10 minutes, then it was allowed to come to room temperature (18–22° C.) spontaneously in about 40 minutes. Finally, it was heated to 38–42° C. and stirred for about 3 hours at this temperature. Product precipitation was observed after about 30 minutes at 38–42° C., leading to formation of an orange suspension. After 3 hours at 38–40° C. the reaction was deemed complete by HPLC analysis calculated by area percent: 90% (sum of oxalic acid intermediate and 5-hydrazinoquinoline). The reaction mixture was cooled to room temperature (18–22° C.) and water (100 ml) was added. The slurry was stirred for 16 hours at 20±2° C., then cooled to 0–2° C. and stirred 1.5 hours at 0–2° C. The product was filtered and washed with methanol (2×30 ml), thus obtaining 107 g of the oxalic acid intermediate as a wet product. A portion of the wet product (97 g) was added to a one liter round-bottomed flask equipped with mechanical stirrer, thermometer, reflux condenser and under a nitrogen atmosphere. Water (100 ml) and concentrated hydrochloric acid (300 ml) were added. The resulting yellow suspension was heated to 90±2° C. and stirred 1.5 hours, maintaining the temperature at 90±2°. The mixture was then cooled to room temperature (20±2° C.) and stirred for two hours at this temperature. The resulting solid was filtered, washed with methanol (3×30 ml) and dried for 16 hours in an air tray drier at 40° C. affording 61.3 g of 5-hydrazinoquinoline dihydrochloride as a yellow crystalline solid.

Example 2

5-Cyclopropyl-1-quinolin-5-yl-1H-pyrazole-4-carboxylic acid

A 200 liter glass-lined reactor under nitrogen was charged with ethyl acetate (51 liters), methyl-3-cyclopropyl-3-oxopropanoate (4.90 kg) and N,N-dimethylformamide dimethylacetal (4.31 kg). The reactor was heated to about 75° C. for four hours. Completion of conversion to α-[(dimethylamino)methylene]-β-oxo-cyclopropanepropanoic acid, (αZ)-methyl ester was confirmed using thin-layer chromatography analysis (ethyl acetate/hexanes,1/1). The reactor was cooled to about 20° C. and the vessel was charged with 5-hydrazinoquinoline dihydrochloride (10.0 kg). Triethylamine (15.0 liters) was added to the reactor over about a one hour period. The reactor was then heated to about 75° C. under nitrogen and maintained at that temperature for four hours. Completion of the formation of 5-cyclopropyl-1-quinolin-5-yl-1H-pyrazole-4-carboxylic acid methyl ester was confirmed by HPLC. The reactor was then cooled to about 20° C. and ethyl acetate (17 liters) was added along with activated carbon (500 g) and filter aid (1.64 kg). A solution consisting of 66 liters of water and citric acid (20.7 kg) was then added. The resulting suspension was agitated for one hour and then filtered. The filter was rinsed with 15 liters of ethyl acetate. The filtrate formed two liquid layers upon standing. The lower, dark red aqueous layer was decanted and discarded. The upper, red organic layer was transferred to a 200 liter glass-lined reactor configured for vacuum distillation. The volume of the red organic layer was reduced by distillation under vacuum to a volume of 25 liters. Propan-2-ol (31 liters) was added to the distillation pot and the volume was reduced by vacuum distillation to 31 liters. A second propan-2-ol (31 liters) charge was made to the distillation pot and the volume was again reduced by vacuum distillation to 34 liters. The distillation apparatus was cooled to about 20° C. and reconfigured for reflux. Aqueous NaOH (50% solution, 6.90 kg) was added to the reconfigured apparatus containing the 5-cyclopropyl-1-quinolin-5-yl-1H-pyrazole-4-carboxylic acid methyl ester/isopropanol solution. The reactor was then heated to about 75° C. under nitrogen and maintained at that temperature for four hours. HPLC analysis of the reaction solution indicated that the conversion to 5-cyclopropyl-1-quinolin-5-yl-1H-pyrazole-4-carboxylic acid was complete. The reactor was then cooled to about 20° C. and the pH of the contents was adjusted to about pH 4 using concentrated hydrochloric acid. A brown suspension of solids formed as the pH was adjusted. The solids were isolated by filtration, rinsed with water and dried under vacuum at about 45° C. resulting in 6.10 kg of 5-cyclopropyl-1-quinolin-5-yl-1H-pyrazole-4-carboxylic acid as a brown solid.

Example 3

Purification of 5-cyclopropyl-1-quinolin-5-yl-1H-pyrazole-4-carboxylic acid

A glass-lined 100 liter reactor was charged with 56 liters of $H_2O$ and 5-cyclopropyl-1-quinolin-5-yl-1H-pyrazole-4-carboxylic acid (5.60 kg). The resulting slurry was adjusted to about pH 12 using 50% aqueous sodium hydroxide. A hazy, red solution formed as the pH was adjusted. Filter aid (500 g) was added to the reactor and the suspension was stirred for more than an hour at about 20° C. Reactor contents were then filtered and the filter was rinsed with water (about 15 L). The filtrate was transferred to a 100 liter glass-lined reactor and the solutions pH was adjusted to about 4 using hydrochloric acid (about 37%). 5-Cyclopropyl-1-quinolin-5-yl-1H-pyrazole-4-carboxylic acid crystallized as a white solid during pH adjustment. The solids were isolated by filtration, rinsed with water and vacuum dried resulting in 5.30 kg of white 5-cyclopropyl-1-quinolin-5-yl-1H-pyrazole-4-carboxylic acid.

1H NMR (DMSO-d6) d 8.94 (dd, J=1.6, 4.0, 1H), 8.15 (dd, J=0.8, 8.4, 1H), 7.87 (s, 1H), 7.85–7.83 (m, 1H), 7.71 (dd, J=1.2, 7.2, 1H), 7.59–7.51 (m, 2H), 1.79 (m, 1H), 0.69 (m, 2H), 0.51–0.47 (m, 2H).

Example 4

5-Cyclopropyl-1-quinolin-5-yl-1H-pyrazole-4-carbonyl chloride

5-Cyclopropyl-1-quinolin-5-yl-1H-pyrazole-4-carboxylic acid (50 g) was slurried in acetonitrile (358 ml) at room temperature in a three-necked round bottom flask under a nitrogen atmosphere. Thionyl chloride (23.4 g) was added dropwise by addition funnel while maintaining the reaction temperature below 20° C. After about 60 minutes, conversion to 5-cyclopropyl-1-quinolin-5-yl-1H-pyrazole-4-carbonyl chloride was confirmed to be complete by HPLC analysis of an aliquot of the reaction mixture that had been quenched with diethylamine. A distillation head and condensor were then attached to the flask, and the reaction was atmospherically distilled at 85° C. to 90% of its original volume. The reaction was then cooled to 0° C. As the mixture was cooled, 5-cyclopropyl-1-quinolin-5-yl-1H-pyrazole-4-carbonyl chloride precipitated from the solution.

Example 5

N-(5-Cyclopropyl-1-quinolin-5-yl-1H-pyrazole-4-carbonyl)-guanidine

In a reaction flask, guanidine HCl (35.1 g) was dissolved in water (268 ml) and 50% NaOH (114.6 g). The acetonitrile/5-cyclopropyl-1-quinolin-5-yl-1H-pyrazole-4-carbonyl chloride mixture of Example 4, was added in three equal portions to the flask containing the guanidine solution while maintaining the reaction temperature below 15° C. throughout the addition. The reaction mixture was brought to room temperature and stirred under nitrogen atmosphere for two hours. The reaction was confirmed to be complete by HPLC. A distillation head and condensor were then attached to the reaction vessel. The product mixture was atmospherically distilled at 85° C. resulting in a slurry having a volume of 400–450 ml. Tetrahydrofuran (THF) (720 ml) was added to the reaction flask and the mixture was warmed to 50–55° C. for 45 minutes and until all all contents had entered solution resulting in an orange biphasic mixture. The mixture was transferred to a separatory funnel and the layers were allowed to separate. The layers were separated and the aqueous layer was extracted with an additional 300 ml of THF. The resulting organic THF layers were combined. Darco® KB-B (5 g) (NORIT Americas Inc., Atlanta, Ga.) and Celite® (5 g) (Celite Corp., Lompoc, Calif.) were added to the THF layers and stirred at room temperature for one hour. The black mixture was vacuum filtered through a #2 Whatman paper filter (Whatman Inc., Clifton, N.J.) and the carbon cake was rinsed with THF. The filtrate was then collected, transferred to a clean flask. and atmospherically distilled at 70° C. to a volume of 450 ml. Ethanol (500 mL) was added to the flask and the mixture was atmospherically distilled at 85° C. to 450 ml. The addition of ethanol and subsequent distillation was repeated three more times. The resulting slurry was cooled to room temperature and allowed to granulate while stirring for three hours. The slurry was then filtered onto a #2 Whatman filter paper and rinsed with THF. The resulting white crystalline solid was allowed to dry for about 48 hours in a vacuum oven at 45 to 50° C. resulting in 52.2 g of N-(5-cyclopropyl-1-quinolin-5-yl-1H-pyrazole-4-carbonyl)-guanidine.

What is claimed is:

1. A method of preparing a compound of formula I'

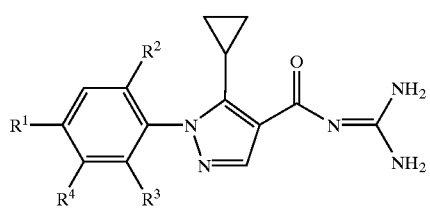

comprising:

combining a mixture of acetonitrile and a compound of formula IX'

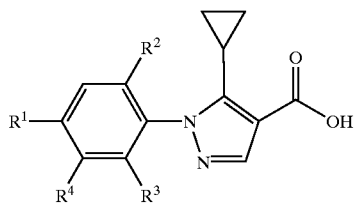

with thionyl chloride to form a mixture comprising a compound of formula X';

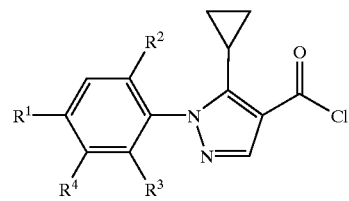

evaporating excess thionyl chloride from said mixture to form an evaporated mixture; and combining said evaporated mixture with guanidine to form a compound of formula I', wherein $R^1$ is methylsulfonyl or hydrogen, $R^2$ is hydrogen or a halogen, $R^3$ is hydrogen, $R^4$ is hydrogen or a halogen, or $R^3$ and $R^4$, together with the carbon atoms to which they are attached, form a six member fully unsaturated ring having one hetero atom that is nitrogen.

2. A method of claim 1, wherein:

said compound of formula IX' is 5-cyclopropyl-1-quinolin-5-yl-1H-pyrazole-4-carboxylic acid;

said compound of formula X' is 5-cyclopropyl-1-quinolin-5-yl-1H-pyrazole-4-carbonyl chloride; and said compound of formula I' is N-(5-cyclopropyl-1-quinolin-5-yl-1H-pyrazole-4-carbonyl)-guanidine.

3. A method of claim 2 wherein said 5-cyclopropyl-1-quinolin-5-yl-1H-pyrazole-4-carboxylic acid in acetonitrile is combined with thionyl chloride at a temperature of about 25° C. for at least about one half hour.

4. A method of claim 3 wherein said 5-cyclopropyl-1-quinolin-5-yl-1H-pyrazole-4-carboxylic acid in acetonitrile is combined with thionyl chloride at a temperature of about 25° C. for at least about one hour.

5. A method of claim 2 wherein said evaporation of thionyl chloride reduces the volume of said mixture by about 10%.

6. A method of claim 2 wherein said evaporation of thionyl chloride is performed under vacuum and at a temperature of about 85° C.

7. A method of claim 2 wherein:

said 5-cyclopropyl-1-quinolin-5-yl-1H-pyrazole-4-carboxylic acid in acetonitrile is combined with thionyl chloride at a temperature of about 25° C. for at least about one hour;

said evaporation of thionyl chloride reduces the volume of said mixture by about 10%; and said removal by evaporation is performed under vacuum and at a temperature of about 85° C.

8. A method of preparing a pharmaceutical composition comprising:

combining a mixture of acetonitrile and a compound of formula IX'

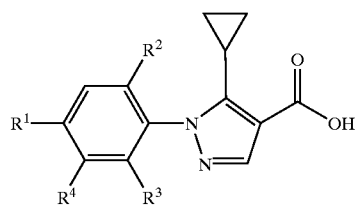

with thionyl chloride to form a mixture comprising a compound of formula X';

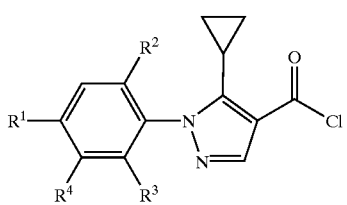

evaporating excess thionyl chloride from said mixture to form an evaporated mixture;

combining said evaporated mixture with guanidine to form a final mixture comprising a compound of formula I'

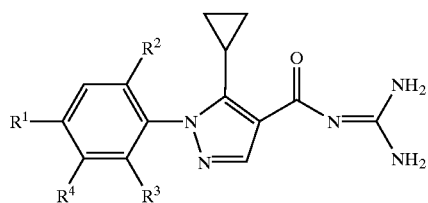

isolating said compound of formula I' from said final mixture; and combining said compound of formula I', or a pharmaceutically acceptable salt thereof, with a pharmaceutically acceptable vehicle, diluent or carrier, wherein $R^1$ is methylsulfonyl or hydrogen, $R^2$ is hydrogen or a halogen, $R^3$ is hydrogen, $R^4$ is hydrogen or a halogen, or $R^3$ and $R^4$, together with the carbon atoms to which they are attached, form a six member fully unsaturated ring having one hetero atom that is nitrogen.

9. A method of claim 8, wherein said compound of formula IX' is 5-cyclopropyl-1-quinolin-5-yl-1H-pyrazole-4-carboxylic acid;

said compound of formula X' is 5-cyclopropyl-1-quinolin-5-yl-1H-pyrazole-4-carbonyl chloride; and said compound of formula I' is N-(5-cyclopropyl-1-quinolin-5-yl-1H-pyrazole-4-carbonyl)-guanidine.

10. A method of claim 8 wherein said 5-cyclopropyl-1-quinolin-5-yl-1H-pyrazole-4-carboxylic acid in acetonitrile is combined with thionyl chloride at a temperature of about 25° C. for at least about one hour.

11. A method of claim 8 wherein said evaporation of thionyl chloride reduces the volume of said mixture by about 10%.

12. A method of claim 8 wherein said removal by evaporation is performed under vacuum and at a temperature of about 85° C.

13. A method of claim 8 wherein, said 5-cyclopropyl-1-quinolin-5-yl-1H-pyrazole-4-carboxylic acid in acetonitrile is combined with thionyl chloride at a temperature of about 25° C. for at least about one hour; and said evaporation of thionyl chloride reduces the volume of said mixture by about 10% and is performed under vacuum and at a temperature of about 85° C.

* * * * *